US012346791B2

(12) United States Patent
Dindin et al.

(10) Patent No.: US 12,346,791 B2
(45) Date of Patent: Jul. 1, 2025

(54) COMPUTER-READABLE RECORDING MEDIUM, ABNORMALITY DETERMINATION METHOD, AND ABNORMALITY DETERMINATION DEVICE

(71) Applicant: FUJITSU LIMITED, Kawasaki (JP)

(72) Inventors: Meryll Dindin, Palaiseau (FR); Yuhei Umeda, Kawasaki (JP); Frederic Chazal, Le Chesnay (FR)

(73) Assignee: FUJITSU LIMITED, Kawasaki (JP)

( * ) Notice: Subject to any disclaimer, the term of this patent is extended or adjusted under 35 U.S.C. 154(b) by 338 days.

(21) Appl. No.: 16/555,254

(22) Filed: Aug. 29, 2019

(65) Prior Publication Data

US 2020/0074281 A1 Mar. 5, 2020

(30) Foreign Application Priority Data

Aug. 31, 2018 (JP) .................. 2018-163968

(51) Int. Cl.
*G06N 3/045* (2023.01)
*A61B 5/318* (2021.01)
*G06F 17/14* (2006.01)
*G06N 3/088* (2023.01)

(52) U.S. Cl.
CPC .............. *G06N 3/045* (2023.01); *A61B 5/318* (2021.01); *G06F 17/142* (2013.01); *G06N 3/088* (2013.01)

(58) Field of Classification Search
CPC ...... G06N 3/0454; G06N 3/088; G06N 3/084; A61B 5/318; A61B 5/363; A61B 5/364; A61B 5/366; A61B 5/7267; G06F 17/142
See application file for complete search history.

(56) References Cited

U.S. PATENT DOCUMENTS 10,441,184 B2 * 10/2019 Baumann ............... A61B 5/361

OTHER PUBLICATIONS

Gebhart, Thomas, and Paul Schrater. "Adversary detection in neural networks via persistent homology." arXiv preprint arXiv:1711.10056 (2017). (Year: 2017).*
Guss, William H., and Ruslan Salakhutdinov. "On characterizing the capacity of neural networks using algebraic topology." arXiv preprint arXiv:1802.04443 (2018). (Year: 2018).*
Berwald, Jesse, Marian Gidea, and Mikael Vejdemo-Johansson. "Automatic recognition and tagging of topologically different regimes in dynamical systems." arXiv preprint arXiv:1312.2482 (2013). (Year: 2013).*

(Continued)

*Primary Examiner* — Miranda M Huang
*Assistant Examiner* — Sidney Vincent Bostwick
(74) *Attorney, Agent, or Firm* — STAAS & HALSEY LLP

(57) ABSTRACT

A learning device performs learning by an autoencoder, using waveform data with changes over time that is obtained from an intrinsic movement of an object. The learning device performs persistent homology conversion to calculate a change in the number of connected component in accordance with a change of a threshold for a value of the first waveform data. The learning device determines abnormality based on a determination result of a learner to which output data of the autoencoder obtained from the waveform data and output data obtained from the persistent homology conversion are input, and in which machine learning about abnormality of the waveform data has been performed.

13 Claims, 9 Drawing Sheets

(56) References Cited

OTHER PUBLICATIONS

Carbonell, Jaime G., Ryszard S. Michalski, and Tom M. Mitchell. "An overview of machine learning." Machine learning (1983): 3-23. (Year: 1983).*
Emrani, Saba. "Physiological Signal Analysis: A Topo-Geometric Perspective." (2016). (Year: 2016).*
Sharov, "Limit Cycles and Chaos", 1996 (obtained from http://alexei.nfshost.com/PopEcol/lec9/chaos.html on Apr. 28, 2023) (Year: 1996).*
Kurtanjek, Želimir. "Principal component ANN for modelling and control of baker's yeast production." Journal of biotechnology 65.1 (1998): 23-35. (Year: 1998).*
Otter, Nina, et al. "A roadmap for the computation of persistent homology." EPJ Data Science 6 (2017): 1-38. (Year: 2017).*
Cole, Alex, and Gary Shiu. "Persistent homology and non-Gaussianity." Journal of Cosmology and Astroparticle Physics 2018. 03 (2018): 025. (Year: 2018).*
Pranav Rajpurkar et al., "Cardiotogist-Level Arrhythmia Detection with Convolutional Neural Networks", arXiv:1707.01836v1 [cs.CV], Jul. 6, 2017.
Mohammad Kachuee et al., "ECG Heartbeat Classification: A Deep Transferable Representation", arXiv:1805.00794v2 [cs.CY], Jul. 12, 2018.

* cited by examiner

COMPUTER-READABLE RECORDING MEDIUM, ABNORMALITY DETERMINATION METHOD, AND ABNORMALITY DETERMINATION DEVICE

CROSS-REFERENCE TO RELATED APPLICATIONS

This application is based upon and claims the benefit of priority of the prior Japanese Patent Application No. 2018-163968, filed on Aug. 31, 2018, the entire contents of which are incorporated herein by reference.

FIELD

The embodiment discussed herein is related to a computer-readable recording medium, an abnormality determination method, and an abnormality determination device.

BACKGROUND

Detection of an abnormal state of movement of an object from waveform data including changes over time in which time series variations of an intrinsic movement of an object, or time series variations when an intrinsic movement is caused according to properties of the object are acquired has been practiced. The intrinsic movement is an intrinsic large variation added to a constant oscillation of a constant value, a micro sine wave, a minute noise, or the like, as an electrocardiographic waveform is observed as periodical heartbeat movement in a micro oscillation. Moreover, the intrinsic movement according to properties is a reaction to stimulation when an object is stimulated in the middle of a steady state.

FIG. 10 illustrates an example of an electrocardiographic waveform. For example, in the case of electrocardiographic waveform, a PQRST form that includes P (small spike), Q (small dip), R (large spike), S (dip), and T (small spike), as illustrated in FIG. 10, is recognized as a basic form. In the case of arrhythmia, the form significantly changes, such as a QRS width being abnormally wide and frequent occurrence of the P wave in short time. Therefore, by determining this form, it is possible to discriminate between a normal electrocardiographic waveform and an abnormal electrocardiographic waveform. As a method of such determination, determination by visual observation has been performed conventionally, but a determination method by using a convolutional neural network (CNN) is used in recent years (Rajpurkar, Pranav; Hannun, Awni Y.; Haghpanahi, Masoumeh; Bourn, Codie; Ng, Andrew Y. "Cardiologist-Level Arrhythmia Detection with Convolutional Neural Networks", arXiv, Jul. 6, 2017, Kachuee, Mohammad; Fazeli, Shayan; Sarrafzadeh, Majid, University of California, Los Angeles (UCLA), "ECG Heartbeat Classification: A Deep Transferable Representation", arXiv, Jul. 12, 2018).

In electrocardiographic waveforms, for example, noises originated from the installation conditions and the measurement conditions of measurement electrodes, variations among individuals of a subject of measurement, and the like are included in electrocardiographic waveform data besides normality and abnormality of heartbeat of a subject. Because noises are also reacted in CNN, it is learned that elements in a specific area have a little effect on the classification. However, as for variations among individuals in noises in an actual situation, a person having an abnormality tends to be more characteristic. Mixture of data including characteristic noises and data including normal noises causes overfitting of the data including characteristic data, to unpreferably affect the determination performance. For this reason, even if CNN is used, the determination accuracy for an electrocardiographic waveform of a subject not included in training data is to be significantly lower than the determination accuracy for an electrocardiographic waveform of a subject included in the training data.

Furthermore, electrocardiographic waveforms are influenced by tachycardia and bradycardia. In the case of a patient of arrhythmia, cycles of the electrocardiographic waveform vary even within the same measurement period. Therefore, even if regularization of electrocardiographic data is attempted, regularization in a form not affecting the abnormality determination is not always performed because forms of PQRST peaks in electrocardiographic waveforms significantly vary among individuals.

SUMMARY

According to an aspect of an embodiment, a non-transitory computer-readable recording medium stores therein a program that causes a computer to execute a process. The process includes performing learning by an autoencoder, using waveform data with changes over time that is obtained from an intrinsic movement of an object; performing persistent homology conversion to calculate a change in number of connected component according to a threshold change in a value direction for the waveform data; and determining abnormality based on a determination result of a learner to which output data of the autoencoder obtained from the waveform data and output data obtained from the persistent homology conversion are input, and in which machine learning about abnormality of the waveform data has been performed.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Preferred embodiments will be explained with reference to accompanying drawings. The embodiments are not intended to limit the present invention. Moreover, respective embodiments can be combined appropriately within a range not causing a contradiction.

[a] First Embodiment

Overall Configuration

Figure 1:
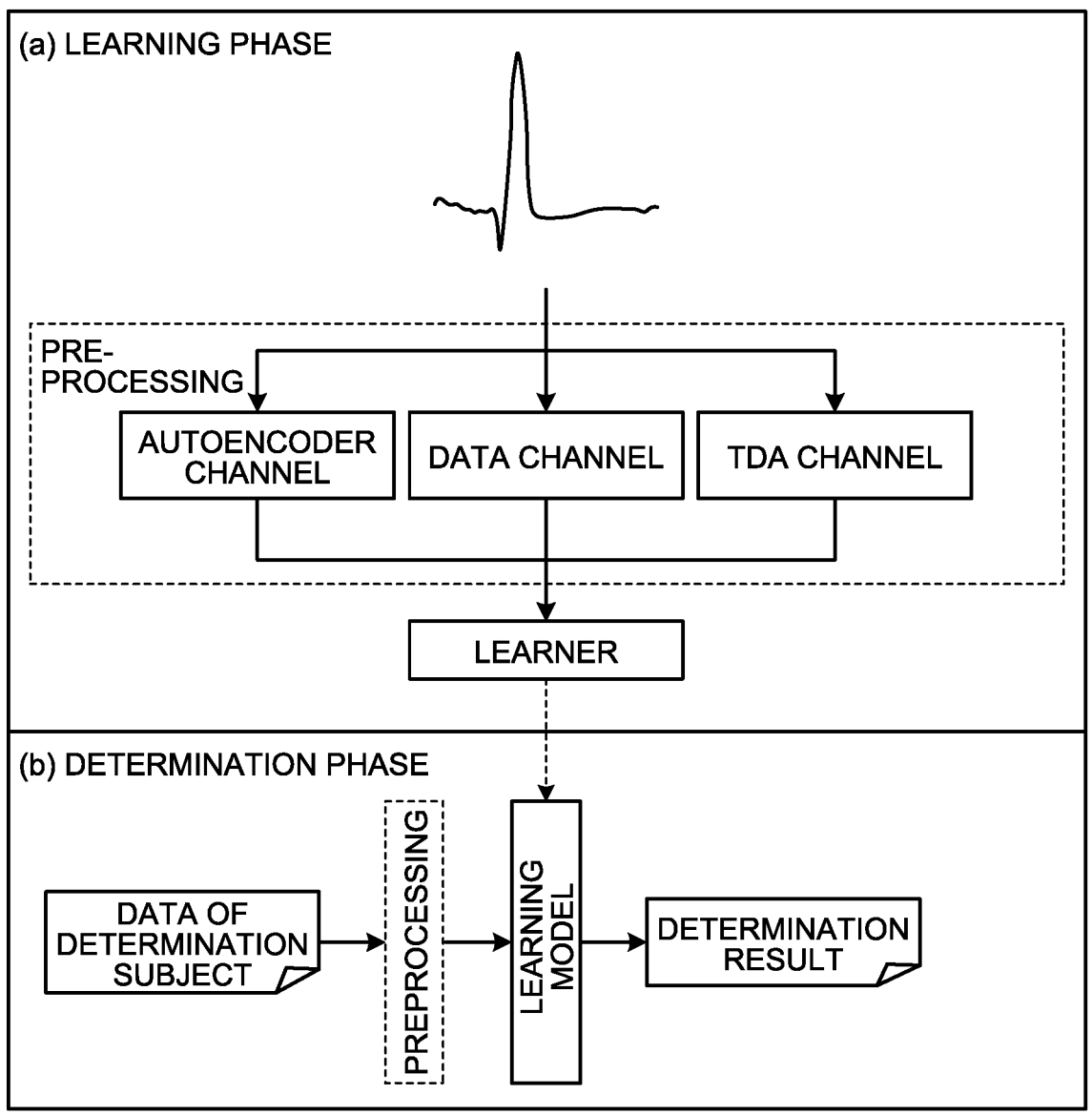
FIG. 1 is a diagram for explaining a learning device according to a first embodiment.

FIG. 1 is a diagram for explaining a learning device according to a first embodiment. The present embodiment is explained, taking heartbeat that is one of fields with increasing applications as an example of waveform data including changes over time. As illustrated in FIG. 1, the learning device is an example of an abnormality determination device that learns a learner that classifies electrocardiographic waveforms as learning data handling electrocardiographic waveform as learning data as one example of waveform data including changes over time, and that performs determination of electrocardiographic waveform data (electrocardiogram) of a subject of determination, to determine abnormality based on a determination result.

In recent years, there is an increasing demand for diagnosis of arrhythmia using electrocardiograms in terms of disease control. On the other hand, because of the increasing number of patients or the many cases of being too late to be treated by the time of diagnosis based on an electrocardiographic waveform, construction of an effective medical system in which simple diagnosis is performed by using a portable electrocardiograph and by diagnosing on software has been expected. For this purpose, construction of a high performance classifier for arrhythmia by machine learning using electrocardiographic waveform as data has been desired.

Such an electrocardiographic waveform basically includes small noises, and how noises are included vary much among individuals. Moreover, because of variations among individuals, such as tachycardia or bradycardia, electrocardiographic waveforms appear to have expanded or contracted horizontal width, but these are the same thing, and it is preferable to be learned not to be determined as different things. However, by a general technique, the learning accuracy is degraded by noises and variations among individuals, and improper determination is concerned.

Figure 2:
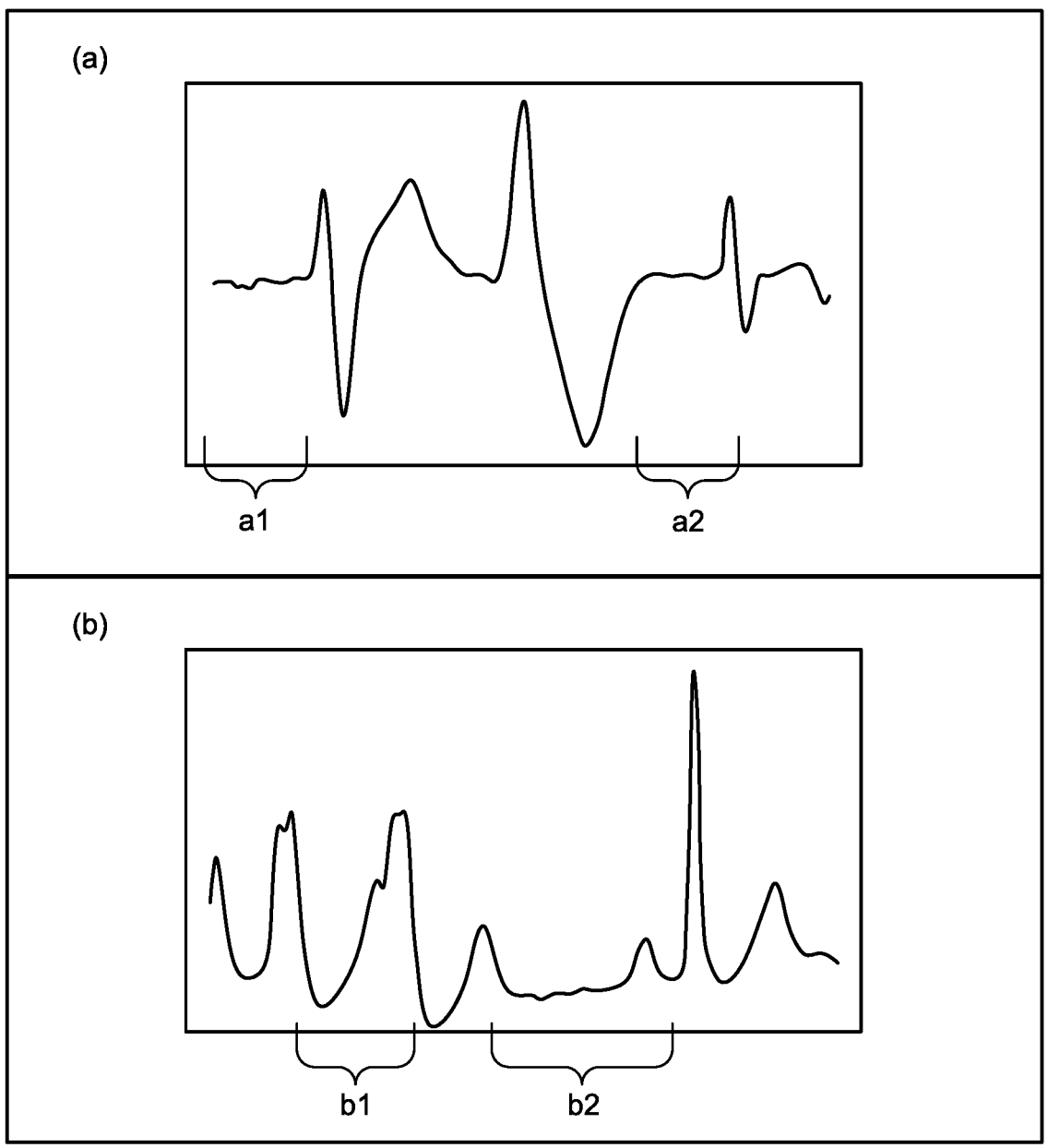
FIG. 2 is a diagram illustrating data example that is difficult to be determined by a general technique.

FIG. 2 is a diagram illustrating data example that is difficult to be determined by a general technique. An electrocardiographic waveform in FIG. 2 is an example of an abnormal electrocardiographic waveform in which a basic form is lost. In the case of (a) in FIG. 2, because noises are included in a flat waveform portions of a1 and a2, a portion of P wave cannot be identified by the general technique. Moreover, in the case of (b) in FIG. 2, intervals between T wave and following P wave vary significantly as in b1 and b2, and it cannot be learned by the general technique unless such learning data is present. That is, in the general technique, a high determination performance is obtained under a condition that the learning data and data to be determined are of the same patient. However, when learning data of an actual use and data to be determined are of different patients, a sufficient determination performance is not obtained.

Therefore, the learning device according to the first embodiment achieves improvement of the determination accuracy by adding an autoencoder channel that is a learning channel using an auto encoder and a TDA channel based on value-filtration to a structure for learning of the learner.

Specifically, the learning device performs learning by the autoencoder using electrocardiographic waveform data. The learning device performs persistent homology conversion to calculate a change in the number of connected components according to a threshold change in a value direction, for electrocardiographic waveform data. The learning device enters output data obtained when the electrocardiographic waveform data is input to the autoencoder and output data obtained from the persistent homology conversion thereto, and performs abnormality determination based on a determination result of the learner that has performed the machine learning about electrocardiographic waveform data and abnormalities.

For example, as illustrated in FIG. 1, the learning device performs preprocessing, when inputting learning data to the learner using CNN, to input data. For example, an autoencoder channel is a form in which an encoder and a decoder that have performed unlabeled unsupervised learning using learning data are incorporated, prior to the entire learning. A data channel is a form of performing fast Fourier transform or extracting a time width (R-R width). A TDA channel is a form of performing the persistent homology conversion to calculate a change in the number of connected components according to a threshold change in a value direction for electrocardiographic waveform, because the autoencoder is not capable of supporting expansion and contraction in a horizontal axis direction (time axis).

As described, the learning device inputs electrocardiographic waveform data being learning data into the autoencoder that has performed learning to extract a feature amount by the autoencoder channel. Moreover, the learning device subjects electrocardiographic waveform data to fast Fourier transform or the like to extract a feature amount by the data channel. Furthermore, the learning device subjects electrocardiographic waveform data to persistent homology conversion by the TDA channel to extracts a feature amount, such as a Betti series. The learning device inputs these feature amounts and the original learning data (electrocardiographic waveform data) to the learner (CNN), to perform learning.

After completion of learning by the learner, the learning device extracts respective feature amounts by using the respective channels for electrocardiographic waveform data of a determination subject, in a similar manner as at the time of learning. The learning device then inputs the respective feature amounts and the electrocardiographic waveform data of a determination subject to the learned learner, and determines whether the electrocardiographic waveform data of a determination subject is abnormal based on an output result from the learner. As a result, the learning device can perform abnormality determination appropriately for electrocardiographic waveform data with changes over time in which a noise is included in either in a time direction and in a value direction.

Functional Configuration

Figure 3:
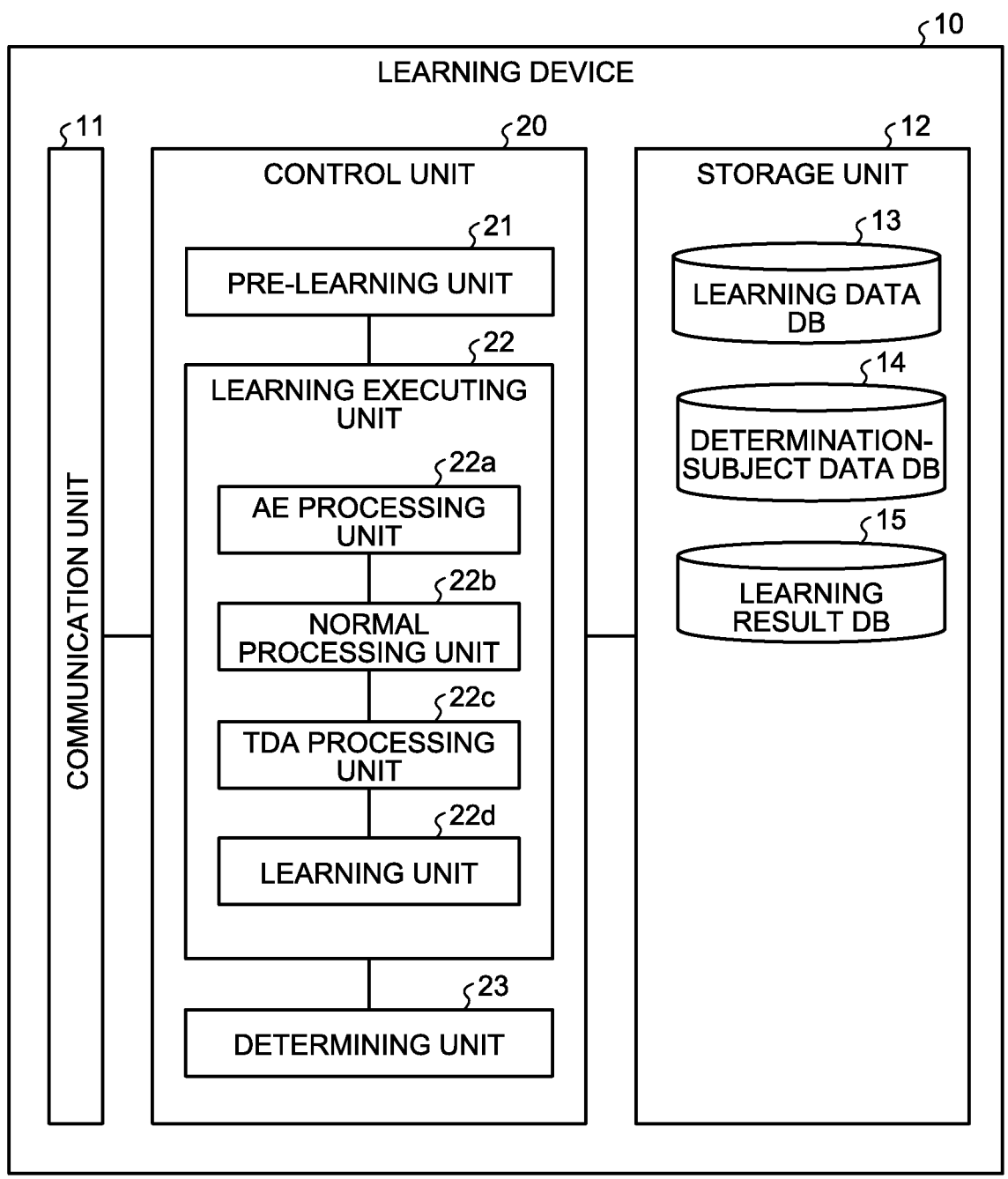
FIG. 3 is a functional block diagram illustrating a functional configuration of the learning device according to the first embodiment.

FIG. 3 is a functional block diagram illustrating a functional configuration of the learning device according to the first embodiment. As illustrated in FIG. 3, a learning device 10 includes a communication unit 11, a storage unit 12, and a control unit 20.

The communication unit 11 is a processing unit that controls communication of other devices. For example, it is a communication interface, or the like. For example, the communication unit 11 receives learning data from an administration terminal, and outputs a learning result, a determination result, and the like to the administration terminal.

The storage unit 12 is an example of a storage device that stores data, a program that is executed by the control unit 20, and the like, and is, for example, a hard disk, a memory, and the like. The storage unit 12 stores a learning data database (DB) 13, a determination-subject data DB 14, a learning result DB 15.

The learning data DB 13 is a database that stores electrocardiographic waveform data of a subject of learning. Specifically, the learning data DB 13 stores normal electrocardiographic waveform data and abnormal electrocardiographic waveform data. A label indicating normal or abnormal can be added to each electrocardiographic waveform data, which is learning data. For example, the learning data DB 13 associates "label, learning data", and stores "normal, electrocardiographic waveform data A" or "abnormal, electrocardiographic waveform data B", and the like. The learning data stored herein is one-dimensional numerical data that is obtained by converting electrocardiographic waveform data into numerals.

The determination-subject data DB 14 is a database that stores electrocardiographic waveform data of a subject of determination. For example, the determination-subject data DB 14 stores electrocardiographic waveform data of a subject of determination whether to be normal or abnormal, not limited to data of the same patient as the learning data. The determination subject data stored herein is also one-dimensional numerical data that is obtained by converting electrocardiographic waveform data into numerals similarly to the learning data.

The learning result DB 15 is a database that stores a learning result. For example, the learning result DB 15 stores a determination result (classification result) of the learning data acquired by the control unit 20, and various kinds of parameters learned by machine learning or the like.

The control unit 20 is a control unit that performs overall control of the learning device 10, and is for example, a processor. The control unit 20 includes a pre-learning unit 21, a learning executing unit 22, and a determining unit 23. The pre-learning unit 21, the learning executing unit 22, and the determining unit 23 are an example of process performed by an electronic circuit included in a processor, a processor, and the like.

The pre-learning unit 21 is a processing unit that learns the autoencoder before learning the learner. Specifically, the pre-learning unit 21 learns the autoencoder by unsupervised learning using normal electrocardiographic waveform data that is stored in the learning data DB 13, and stores a result of learning in the learning result DB 15.

Figure 4:
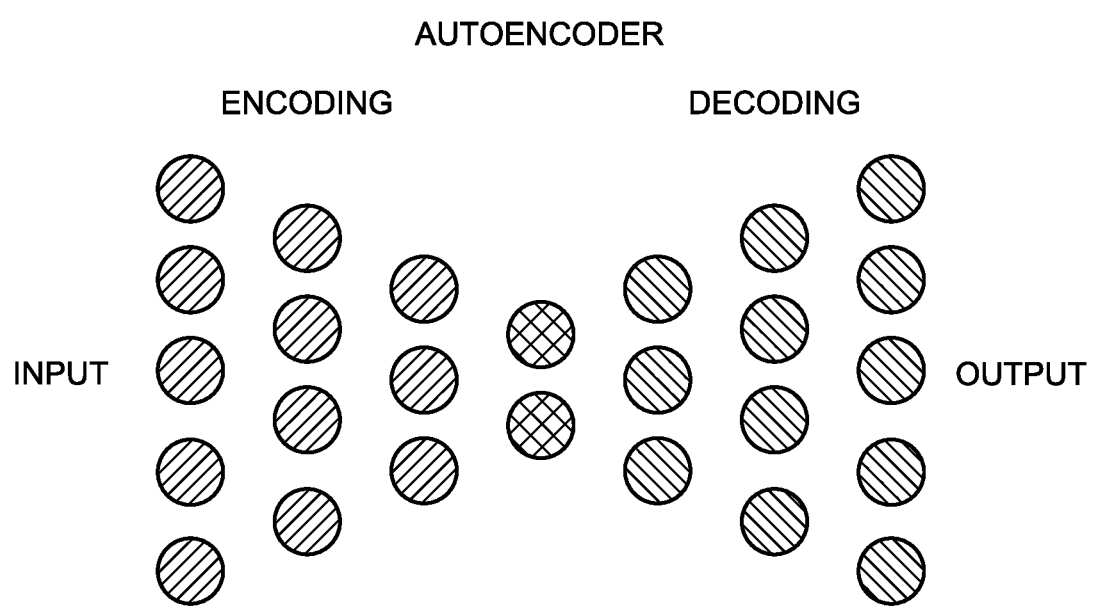
FIG. 4 is a diagram for explaining processing by an autoencoder.

FIG. 4 is a diagram for explaining processing by the autoencoder. As illustrated in FIG. 4. the autoencoder is a sort of a neural network, and is to acquire a feature expression with reduced data amount. If a feature compressed by an encoder can be reconstructed by an encoder, potential variables (a feature expression, a feature amount, and the like) without an unnecessary dimension of input data can be acquired.

Therefore, the pre-learning unit 21 learns the autoencoder such that data subjected to dimension compression and then reconstructed can be restored as much as possible. For example, the pre-learning unit 21 calculates a reconstruction error by comparing input data and output data so that the both data match with each other, and adjusts weights of two neural networks of the encoder and the decoder by backpropagation.

The timing of ending the learning can be arbitrarily set to a point of time when learning with equal to or more than the predetermined number of pieces of learning data has been finished, when the reconstruction error becomes smaller than a threshold, or the like. The autoencoder thus learned is structured to hold important information of the original data with small amount of information and, therefore, serves as a high-performance noise removal function with respect to a time series.

The learning executing unit 22 includes an AE processing unit 22a, a normal processing unit 22b, a TDA processing unit 22c, and a learning unit 22d, and is a processing unit that learns the learner using CNN. The AE processing unit 22a corresponds to the autoencoder channel in FIG. 1, the normal processing unit 22b corresponds to the data channel, and the TDA processing unit 22c corresponds to the TDA channel.

The AE processing unit 22a is a processing unit that extracts a feature amount by using the learned autoencoder that has been learned by the pre-learning unit 21. For example, the AE processing unit 22a constructs an autoencoder in which learned parameters stored in the learning result DB 15 are set. The AE processing unit 22a acquires the learning data, "electrocardiographic waveform data A" to which the label, "normal" is added from the learning data DB 13, to input to the autoencoder. Thereafter, the AE processing unit 22a acquires an output value from the autoencoder, and inputs an acquired output value to the learning executing unit 22.

The normal processing unit 22b is a processing unit that performs processing similar to general learning of CNN, and performs fast Fourier transform and the like. Explaining with the above example, the normal processing unit 22b acquires the learning data, "electrocardiographic waveform data A" to which the label, "normal" is added from the learning data DB 13.

The normal processing unit 22b inputs the read data itself to the learning unit 22d. Moreover, the normal processing unit 22b inputs a calculation result obtained by performing the fast Fourier transform on the acquired learning data, "electrocardiographic waveform data A", to the learning unit 22d. Furthermore, the normal processing unit 22b extracts a time width and the like from the learning data, "electrocardiographic waveform data A", to input to the learning unit 22d. As described, the normal processing unit 22b inputs a calculation result form fast Fourier transform, a time width, and data itself to the learning unit 22d.

The TDA processing unit 22c is a processing unit that performs persistent homology conversion to calculate a change in the number of connected components according to a threshold change in a value direction, for learning data. Explaining with the above example, the TDA processing unit 22c acquires the learning data, "electrocardiographic waveform data A" to which the label, "normal" is added from the learning data DB 13. The TDA processing unit 22c then performs persistent homology conversion using value-based filtration on the learning data, "electrocardiographic waveform data A", to generate a Betti series. Thereafter, the TDA processing unit 22c inputs the Betti series to the learning unit 22d.

The persistent homology is more specifically explained. First, "homology" is a method of expressing features of an object by the number of holes in m (m≥0) dimensions. The "hole" herein is an element of a homology group, and a zero-dimensional hole is a connected component, a one-dimensional hole is a hole (tunnel), and a two-dimensional hole is a void. The number of holes of each dimension is called Betti number. The "persistent homology" is a method of characterizing transition of m-dimensional holes of an object (in this example, point cloud), and a feature relating to arrangement of points can be learned by using the persistent homology. In this method, each point in an object is gradually expanded into a spherical shape, and a time when each hole is born in this process (expressed by a radius of a sphere at the time of birth) and a time when it dies (expressed by a radius of the sphere at the time of death) are identified.

In the calculation process of the persistent homology, a birth radius and a death radius of an element (that is, a hole) of a homology group are calculated. By using the birth radius and the death radius, barcode data can be generated. The barcode data is generated for each hole dimension. Therefore, by combining barcode data of plural hole dimensions, one block of barcode data can be generated. Series data is data that represents a relationship between a radius (that is, time) of a sphere in persistent homology and a Betti number.

While zero dimension, one dimension, and two dimensions are subjects to process in general persistent homology described above, only a connected component, which is a zero-dimensional hole, is a subject to process in the present embodiment.

Figure 5:
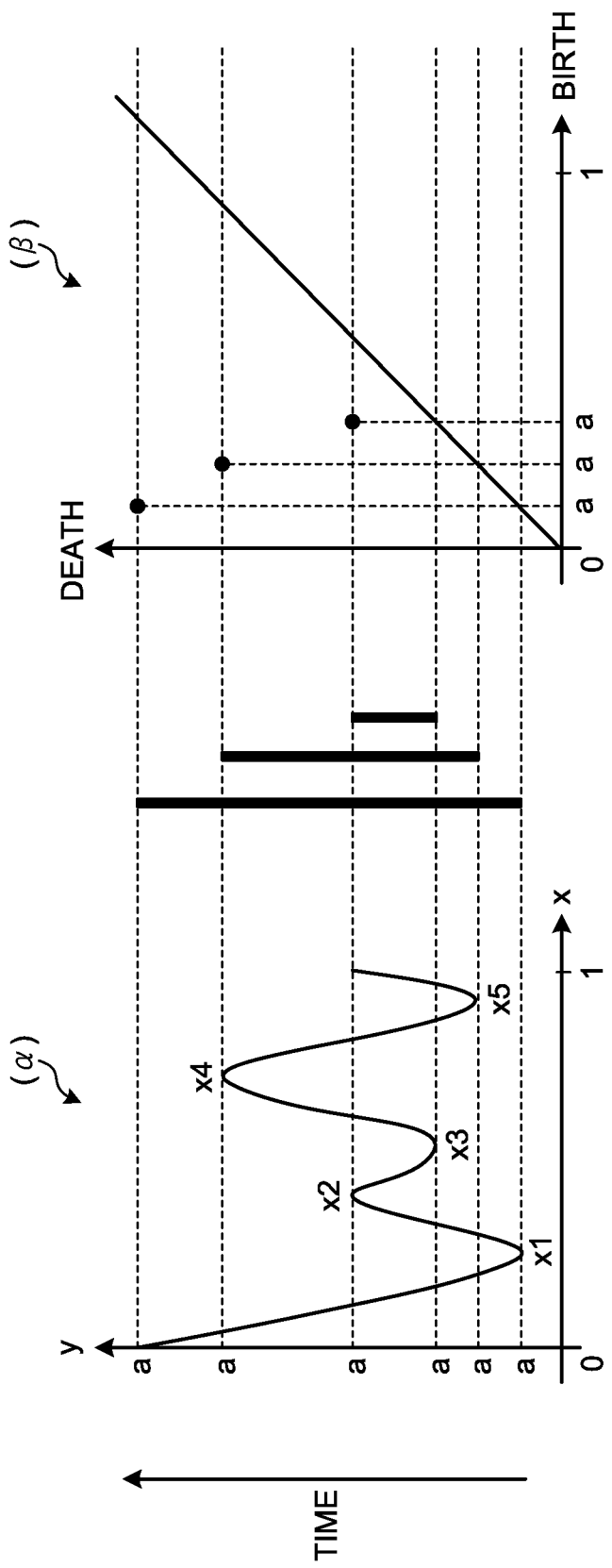
FIG. 5 is a diagram for explaining topological data analysis (TDA) processing.

Next, processing by the TDA processing unit 22c is specifically explained. FIG. 5 is a diagram for explaining the TDA processing. As illustrated in (α) in FIG. 5, the TDA processing unit 22c increases a threshold uniformly from a side with a small numeric value, and counts the number of connected components, which are zero-dimensional holes. For example, the TDA processing unit 22c finds that an associated component is generated at a point of x1, and a connected component is then generated at a point of x5, and an associated component is generated at a point of x3. The TDA processing unit 22c determines that a connection generated later has died because the connected components are coupled at a point of x2, and determines that a connection generated later has died because connected components are coupled at a point x4 also.

As described, the TDA processing unit 22c regards it as birth when a new connected component is generated, and regards that one has died (death) when connected components are coupled, and generates (β) in FIG. 5 depicting birth and death timing. Similarly, the TDA processing unit 22c decreases the threshold uniformly from a side with a large numeric value, counts the number of associated components, and counts the number of birth and death of connected components.

Figure 6:
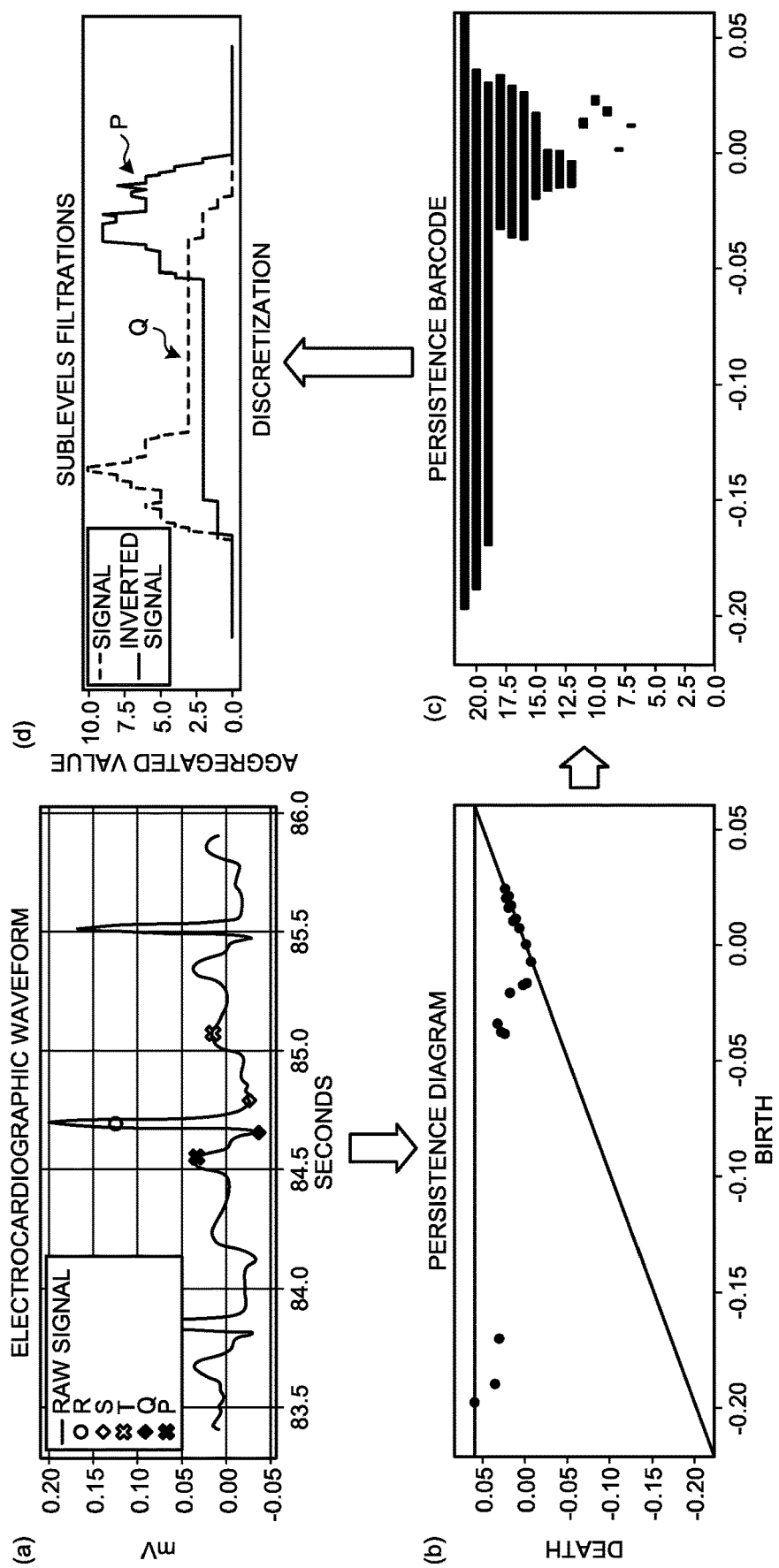
FIG. 6 is a diagram for explaining processing of generating a Betti series from an electrocardiographic waveform.

Thereafter, the TDA processing unit 22c performs generation of barcode data and generation of a Betti series. FIG. 6 is a diagram for explaining processing of generating a Betti series from an electrocardiographic waveform. As illustrated in FIG. 6, the TDA processing unit 22c increases the threshold uniformly from a side with a small numeric value for electrocardiographic waveform data having the PQRST form illustrated in (a) in FIG. 6, and counts the number of connected components, which are zero-dimensional holes ((b) in FIG. 6).

Subsequently, the TDA processing unit 22c generates barcode data using a counting result of the connected components by the method described above ((c) in FIG. 6). In (d) in FIG. 6, series data P when processed from a small numeric value and series data Q when processed form a large numeric value are given.

A graph in (c) in FIG. 6 is a graph that is generated from barcode data, and a horizontal axis indicates a radius. A graph in (d) in FIG. 6 is a graph that is generated from series data (described as Betti series in some cases), and a vertical axis indicates a Betti number. As described above, the Betti number expresses the number of holes and, for example, when the number of holes that are present at the time of a radius at one point in the graph of (c) in FIG. 6 is 10, the Betti number corresponding to the one time in the graph of (d) in FIG. 6 is also 10. The Betti number is counted per block. Note that as the graph of (d) in FIG. 6 is a graph of pseudo time series data, a value of the horizontal axis itself is not significant.

Referring back to FIG. 3, the learning unit 22d is a processing unit that performs learning of CNN being a learner. Specifically, the learning unit 22d performs CNN learning by supervised learning using labeled learning data stored in the learning data DB 13.

An example of performing learning by using the learning data, "electrocardiographic waveform data A" to which the label "normal" is added is explained. The learning unit 22d acquires an output value of the autoencoder, a calculation result of fast Fourier transform, a time width, a Betti series, and the electrocardiographic waveform data A itself from the respective processing units 22a to 22c, to input to CNN. The learning unit 22d then compares an output result of CNN and the label, "normal", and learns CNN by backpropagation or the like to reduce an error.

When learning of CNN is completed, the learning unit 22d stores respective parameters in CNN in the learning result DB 15 as a learning result. Timing of finishing learning can be arbitrarily set to a point when learning using the predetermined number of or more pieces of learning data has finished, a point when the reconstruction threshold has become smaller than a threshold, or the like.

The determining unit 23 is a processing unit that performs abnormal determination of electrocardiographic waveform data of a determination subject, by using a learned learning model. Moreover, the determining unit 23 stores a determination result in the storage unit 12, display it on a display unit, such as a display, and transmits it to the administration terminal.

For example, the determining unit 23 reads the various kinds of parameters stored in the learning result DB 15, and constructs a learning model by CNN in which the various kinds of parameters are set. The determining unit 23 then reads electrocardiographic waveform data of a determination subject from the determination-subject data DB 14.

Subsequently, the determining unit 23 performs the same processing as the AE processing unit 22a, the normal processing unit 22b, and the TDA processing unit 22c on the electrocardiographic waveform data of a determination subject, and acquires an output value of the autoencoder, a calculation result of fast Fourier transform, a time width, and a Betti series. The determining unit 23 then inputs the respective feature amounts and the electrocardiographic waveform data itself of a determination subject into the learning model (CNN), and acquires a determination result. Thereafter, the determining unit 23 determines whether the electrocardiographic waveform data of a determination subject is normal or abnormal based on the determination result. For example, the determining unit 23 determines that the electrocardiographic waveform data of a determination subject as normal when a probability of being normal is higher out of a probability of being normal and a probability of being abnormal indicated in the determination result, and determines that the electrocardiographic waveform data of a determination subject as abnormal when the probability of being abnormal is higher.

Flow of Processing

Figure 7:
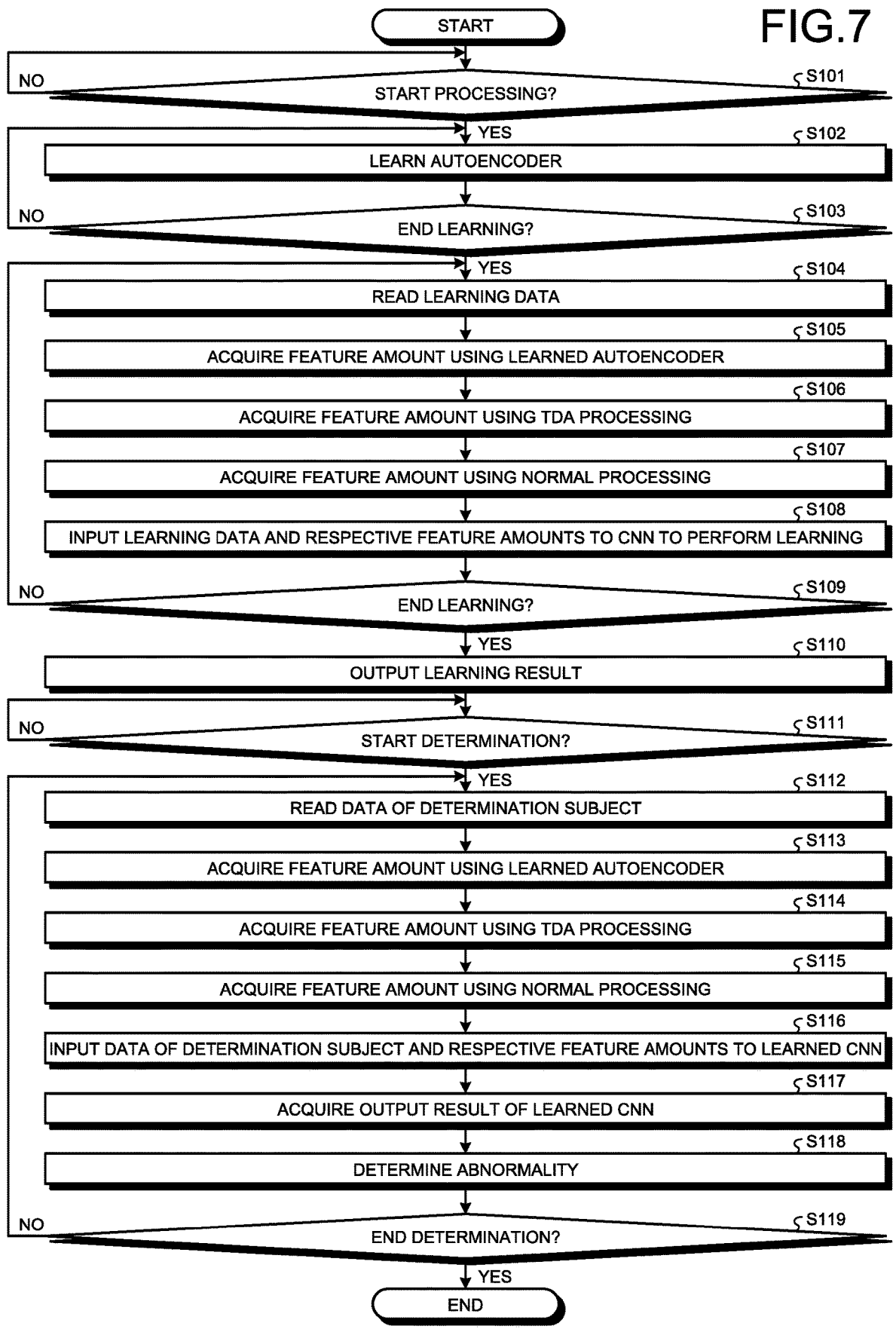
FIG. 7 is a flowchart illustrating a flow of processing.

Next, a flow of the determination processing described above is explained. FIG. 7 is a flowchart illustrating a flow of the processing. As illustrated in FIG. 7, when the processing is started (S101: YES), the pre-learning unit 21 of the learning device 10 learns the autoencoder by unsupervised learning using normal learning data (S102).

Subsequently, the pre-learning unit 21 repeats the learning until learning of the autoencoder is finished (S103: NO), and when the learning of the autoencoder by the pre-learning unit 21 is completed (S103: YES), the learning executing unit 22 reads labeled learning data from the learning data DB 13 (S104).

The AE processing unit 22a inputs learning data to the learned autoencoder, and acquires an output result of the autoencoder as a feature amount (S105). Subsequently, the TDA processing unit 22c performs persistent homology conversion of the learning data, and acquires a Betti series as a feature amount (S106). Moreover, the normal processing unit 22b performs fast Fourier transform and the like on the learning data, and acquires a calculation result of the fast Fourier transform, a time width, and the like as feature amounts (S107). Note that S105 to S107 are performed in any order.

The learning unit 22d inputs the respective feature amounts acquired at S105 to S107 and the learning data to CNN, and performs supervised learning based on the label added to the learning data for CNN (S108). Thereafter, the learning unit 22d repeats the processing at S104 and later when learning is to be continued (S109: NO), and outputs a leaning result to the learning result DB 15 (S110) when the learning is ended (S109: YES).

Thereafter, when an instruction to start the determination processing is received (S111: YES), the determining unit 23 reads data of a determination subject from the determination-subject data DB 14 (S112). Subsequently, the determining unit 23 inputs the data of a determination subject to the learned autoencoder, and acquires an output result of the autoencoder as a feature amount (S113), performs persistent homology conversion of the learning data to acquire a Betti series as a feature amount (S114), and performs fast Fourier transform and the like on the learning data to acquire a calculation result of the fast Fourier transform, a time width, and the like as feature amounts (S115). Note that S113 to S115 are performed in any order.

The determining unit 23 inputs the respective feature amounts acquired at S113 to S115 and the data of a determination subject to the learned learning model (CNN) (S116), and acquires an output result (S117). Thereafter, the determining unit 23 performs abnormality determination based on the output result (S118). Thereafter, the determining unit 23 repeats the processing at S112 and later when determination is to be continued (S119: NO), and ends the determination processing when the determination is ended (S119: YES).

Effect

As described above, for noise removal, by incorporating the autoencoder channel, precise general-purpose noise removal becomes possible without performing settings per data as in the method of moving average. Moreover, when it is applied to electrocardiographic waveform data, because a PQRST form that fluctuates greatly than noises is included, it is highly effective in removing noises compared to time series data in which up-and-down movement is repeated within the same range.

Furthermore, as for variations among individuals in an electrocardiographic waveform caused by tachycardia or bradycardia, by providing a TDA channel, a learning model enabling accurate determination (classification) can be constructed without complicated settings. Generally, in the case of a patient of tachycardia or bradycardia, for example, even if positions of R are aligned, positions of P, Q, S, T vary largely, it is recognized as different data because the deviation in positions is too large for regular CNN. Particularly, a patient having abnormality tends to have extreme tachycardia or bradycardia, and a patient having so extreme tachycardia or bradycardia that it is not found in the learning data cannot be classified appropriately. Moreover, because a patient having tachycardia or bradycardia of a level not found in the learning data is classified based on the degree of tachycardia or bradycardia, the determination is not related to arrhythmia, resulting in degraded performance. To cope with this problem, it is reqested to perform scaling appropriately, or to collect sufficient amount of data of all kinds of tachycardia or bradycardia, but these are not practical.

In the value-based filtration by the TDA channel, a result dependent only on changes in an observation value direction is obtained and, therefore, the same output is obtained as for results of those expanded or contracted in the time axis direction. Furthermore, in the value-based filtration, influences of small noises and the like gather on a diagonal line, and a small deviation in shape is recognized as a small deviation of a point on a diagram. As a result, it is possible to automate scaling, and to perform learning in which classification is determined by a shape of rough waveform and that does not interfere characteristics of arrhythmia.

Figure 8:
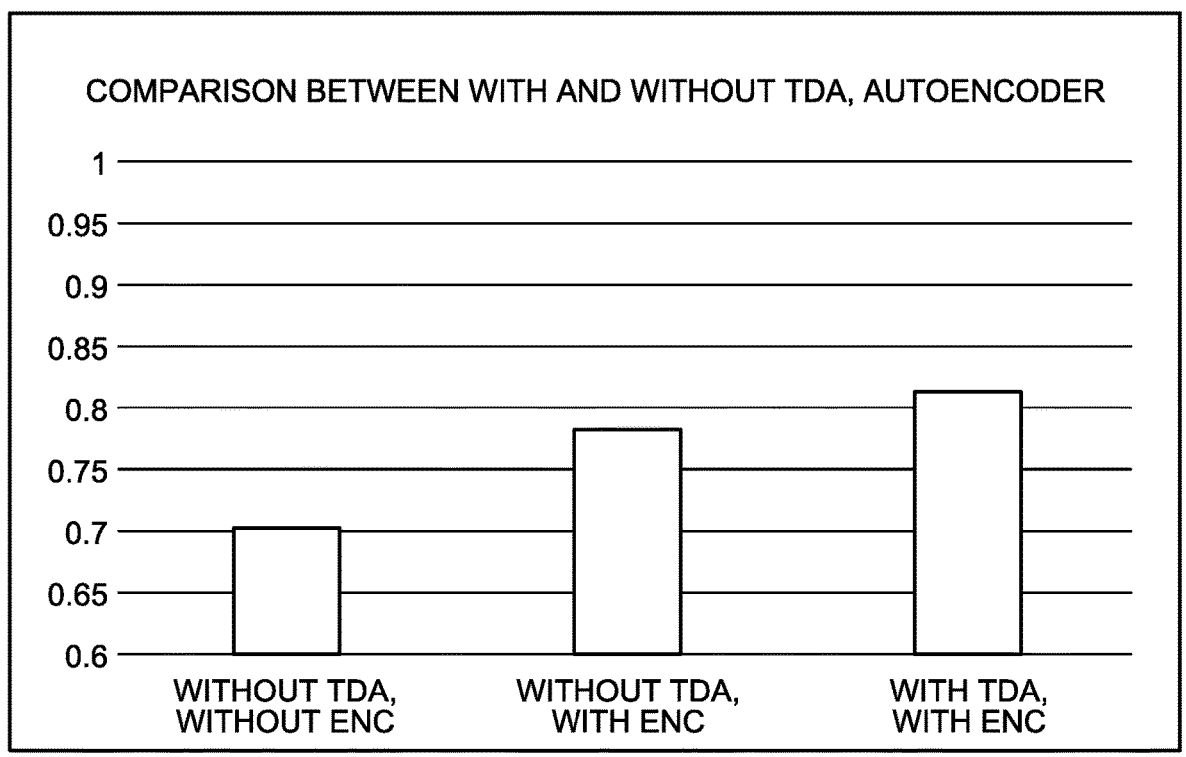
FIG. 8 is a diagram for explaining a result of comparison with a general technique.

FIG. 8 is a diagram for explaining a result of comparison with a general technique. A vertical axis in FIG. 8 is for an accuracy rate, and is a rate of determining normal electrocardiographic waveform data as normal and abnormal electrocardiographic waveform data as abnormal. As illustrated in FIG. 8, while the accuracy rate of a general CNN learning without the TDA channel nor autoencoder (END) was 70%, the accuracy rate improved by adding the END channel, and further improved by also adding the TDA channel.

From the above result, it is found that the learning device 10 can perform abnormality determination appropriately on waveform data with changes over time including noises, by incorporating the autoencoder channel and the TDA channel in the general CNN processing (data channel).

[b] Second Embodiment

The embodiment of the present invention has been explained, but the present invention can be implemented by various different forms other than the embodiment described above.

Time Series Data

In the above embodiment, an electrocardiographic waveform has been used as an example of series data including changes over time, but it is not limited to this kind of time series data. For example, it can be living body data (time series data of brain waves, pulse, body temperature, or the like), data of a wearable sensor (time series data of a gyro sensor, a geomagnetic sensor, or the like), financial data (time series data of interest, prices, a balance of international payments, stock prices, or the like), natural environment data (time series data of atmospheric temperature, humidity, carbon dioxide level, or the like), social data (time series data of labor statistics, population statistics, or the like), and the like.

Channel Structure

In the above embodiment, an example of incorporating an autoencoder channel and a TDA channel has been explained, but it is not limited thereto, and it can be structured to incorporate only either one of the autoencoder channel and the TDA channel.

Learning Model

In the above embodiment, an example of using CNN has been explained, but it is not limited thereto and various kinds of neural networks, such as recurrent neural networks (RNN), can be used, and another machine learning can be adopted. Moreover, as for a learning method also, various publicly-known methods other than backpropagation can be adopted. Furthermore, the neural network has a multilayer structure constituted of an input layer, a middle layer (hidden layer), and an output layer, and each layer has a structure in which nodes are connected by edges. Each layer has a function called "activation function", and an edge has a "weight", and a value of each node is calculated from a value of a node on a previous layer, a value of a weight of a connecting edge (weighting factor), and an activation function of the layer. As for a calculation method, various publicly-known methods can be adopted.

Moreover, learning in a neural network is to correct parameters, that is, weights and biases, to obtain a proper value of an output layer. In the backpropagation, a "loss function" that indicates how far a value of the output layer is deviated from a proper state (desired state) is determined for the neural network, and weights and biases are updated to minimize the loss function by using gradient descent, and the like.

System

The processing procedure, the control procedure, specific names, and various kinds of information including data and parameters can be arbitrarily changed unless otherwise specified.

Each component of each device illustrated in the drawings is a functional idea and thus is not always configured physically as illustrated in the drawings. That is, specific forms of distribution and integration of the respective devices are not limited to the ones illustrated. That is, all or part thereof can be configured to be distributed or integrated functionally or physically in arbitrary units according to various kinds of loads, usage conditions, and the like. For example, learning and determination can be configured with separate devices, such as a learning device that includes the pre-learning unit 21 and the learning executing unit 22 and a determination device that includes the determining unit 23.

Furthermore, as for the respective processing functions performed by the respective devices, all or arbitrary part thereof can be implemented by a central processing unit (CPU) and a computer program that is analyzed and executed by the CPU, or can be implemented as hardware by wired logic.

Hardware

Figure 9:
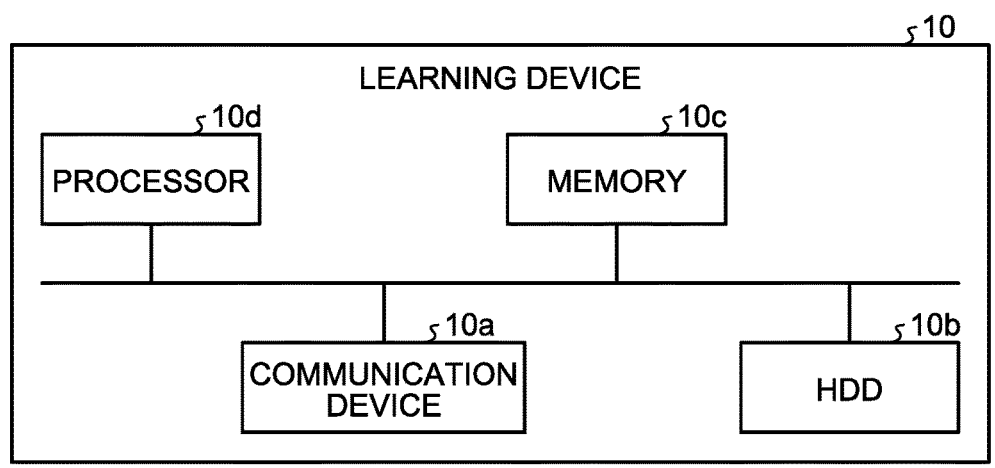
FIG. 9 is a diagram for explaining a hardware configuration example.
Figure 10:
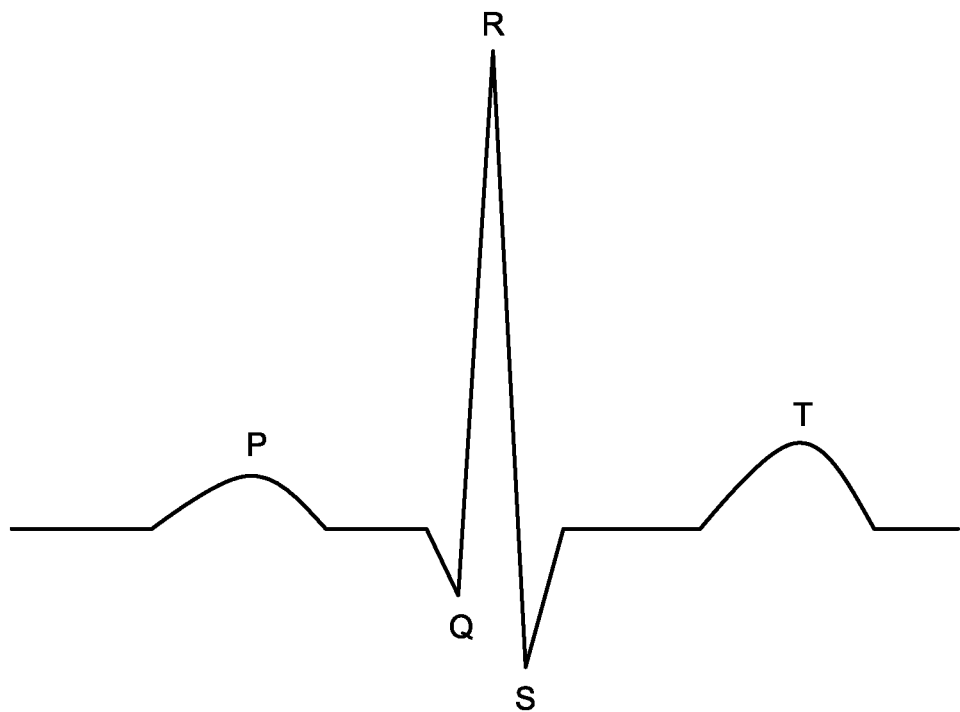
FIG. 10 is a diagram illustrating an example of an electrocardiographic waveform.

FIG. 9 is a diagram for explaining a hardware configuration example. As illustrated in FIG. 9, the learning device 10 includes a communication device 10a, a hard disk drive (HDD) 10b, a memory 10c, and a processor 10d. Moreover, the respective components illustrated in FIG. 9 are connected with each other through a bus or the like.

The communication device 10a is a network interface card, or the like, and communicates with other servers. The HDD 10b stores a program to activate the functions and the DBs illustrated in FIG. 3.

The processor 10d reads programs to implement processing similar to the respective processing units illustrated in FIG. 3 from the HDD 10b or the like to develop them on the memory 10c, thereby operating a process to perform the respective functions explained in FIG. 3 and the like. That is, this process performs a function similar to the respective functions included in the learning device 10. Specifically, the processor 10d reads programs having functions similar to those of the pre-learning unit 21, the learning executing unit 22, the determining unit 23, and the like from the HDD 10b or the like. The processor 10d then performs the process to perform the processing similar to those of the pre-learning unit 21, the learning executing unit 22, the determining unit 23, and the like.

As described, the learning device 10 functions as an information processing apparatus that performs an abnormality determination method by reading and executing a program. Moreover, the learning device 10 can also implement the functions similar to those in the above embodiment by reading the program described above from a recording medium by a medium reader device, and by executing the read program. Note that the program in the other embodiment is not limited to be executed by the learning device 10. For example, the present invention can be similarly applied also when the program is executed by another computer or server, or when the program is executed by those in cooperation.

According to one aspect, abnormality determination for waveform data with changes over time including noises can be appropriately performed.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A non-transitory computer-readable recording medium having stored therein a program that causes a computer to execute a process comprising:
   acquiring first data from a trained autoencoder by inputting, into the autoencoder, first waveform data of waveforms that have variations among individuals;
   generating second data by applying persistent homology conversion to the first waveform data in accordance with a change of a threshold value for a value of the first waveform data;
   training a machine learning model by inputting the first waveform data, the first data and the second data into the machine learning model;
   wherein the applying persistent homology conversion to the first waveform data includes:
      a process of first counting the number of connected components, which are zero-dimensional holes by decreasing the threshold value uniformly for the first waveform data, and
      outputting series data, indicating a transition of a number of connected components, based on a result of the process of first counting; and
      a process of second counting the number of connected components, which are zero-dimensional holes by increasing the threshold value uniformly for the first waveform data, and
      outputting series data, indicating a transition of a number of connected components, based on a result of the process of second counting, and
      the machine learning model is used for a process of determining abnormality for second waveform data based on an output result acquired by inputting second waveform data, third data and fourth data into the machine learning model, the third data being acquired by inputting the second waveform data into the autoencoder, the fourth data being generated by applying persistent homology conversion to the second waveform data.

2. The non-transitory computer-readable recording medium according to claim 1, wherein
the process of determining includes further input of any one of the third data and the fourth data and a calculation result obtained by performing fast Fourier transform on the first waveform data to a learner, and determine abnormality based on a determination result output by the learner.

3. The non-transitory computer-readable recording medium according to claim 1, wherein
the process of determining includes converting a result of the persistent homology conversion into a Betti series to input to a learner, and determining abnormality based on a determination result output by the learner.

4. The non-transitory computer-readable recording medium according to claim 1, wherein the process of determining is implemented by a learner which is a convolutional neural network.

5. The non-transitory computer-readable recording medium according to claim 1, wherein
the acquiring the first data from the autoencoder occurs by unsupervised learning with normal waveform data.

6. The non-transitory computer-readable recording medium according to claim 1, the process further comprising:
performing machine learning of a learner by supervised learning with the first waveform data that is learning data to which a label indicating either one of normal and abnormal is added.

7. An abnormality determination method comprising:
acquiring first data from a trained autoencoder by inputting, into the autoencoder, first waveform data of waveforms that have variations among individuals;
generating second data by applying persistent homology conversion to the first waveform data in accordance with a change of a threshold value for a value of the first waveform data;
training a machine learning model by inputting the first waveform data, the first data and the second data into the machine learning model;
wherein the applying persistent homology conversion to the first waveform data includes:
a process of first counting the number of connected components, which are zero-dimensional holes by decreasing the threshold value uniformly for the first waveform data, and
outputting series data, indicating a transition of a number of connected components, based on a result of the process of first counting; and
a process of second counting the number of connected components, which are zero-dimensional holes by increasing the threshold value uniformly for the first waveform data, and
outputting series data, indicating a transition of a number of connected components, based on a result of the process of second counting, and
the machine learning model is used for a process of determining abnormality for second waveform data based on an output result acquired by inputting second waveform data, third data and fourth data into the machine learning model, the third data being acquired by inputting the second waveform data into the autoencoder, the fourth data being generated by applying persistent homology conversion to the second waveform data.

8. The abnormality determination method according to claim 7, wherein
the process of determining includes further input of any one of the third data and the fourth data and a calculation result obtained by performing fast Fourier transform on the first waveform data to a learner, and determine abnormality based on a determination result output by the learner.

9. The abnormality determination method according to claim 7, wherein
the process of determining includes converting a result of the persistent homology conversion into a Betti series to input to a learner, and determining abnormality based on a determination result output by the learner.

10. The abnormality determination method according to claim 7, wherein the process of determining is implemented by a learner which is a convolutional neural network.

11. The abnormality determination method according to claim 7, wherein
the acquiring the first data from the autoencoder occurs by unsupervised learning with normal waveform data.

12. The abnormality determination method according to claim 7, further comprising:
performing machine learning of a learner by supervised learning with the first waveform data that is learning data to which a label indicating either one of normal and abnormal is added.

13. The non-transitory computer-readable recording medium according to claim 1, wherein
the first waveform data is an electrocardiographic waveform that indicates normality and abnormality of heartbeat of an object among the plurality of objects.

* * * * *